United States Patent [19]

Freeman

[11] 4,448,190

[45] May 15, 1984

[54] CONTROL SYSTEM FOR BODY ORGANS

[76] Inventor: Maynard L. Freeman, 5469 Ranier Dr., Lisle, Ill. 60532

[21] Appl. No.: 285,302

[22] Filed: Jul. 20, 1981

Related U.S. Application Data

[63] Continuation-in-part of Ser. No. 34,224, Apr. 30, 1979, Pat. No. 4,304,225.

[51] Int. Cl.³ .............................................. A61H 31/00
[52] U.S. Cl. ...................................... 128/60; 128/1 D
[58] Field of Search .................................. 128/54–55, 128/58, 60, 62 R, 63, 1 D, 327, 686, 132 R, 202.12

[56] References Cited

U.S. PATENT DOCUMENTS

| | | | |
|---|---|---|---|
| 1,953,424 | 4/1934 | Miller | 128/63 |
| 3,034,501 | 5/1962 | Hewson | 128/60 X |
| 3,454,010 | 7/1969 | Lilligren et al. | 128/327 |
| 3,505,987 | 4/1970 | Heilman | 128/1 D |
| 3,955,563 | 5/1976 | Maione | 128/55 X |
| 4,066,084 | 1/1978 | Tillander | 128/327 |
| 4,304,225 | 12/1981 | Freeman | 128/60 |

OTHER PUBLICATIONS

Tanabe et al., "Wall Reinforcement with Highly Porous Dacron Mesh in Aortic Surgery", *Ann. Surg.*, 4-1980, pp. 452-455.
Birtwell et al., "The Evolution of Counterpulsation Techniques", *Medical Instrumentation*, vol. 10, No. 5, 9-10/1976.
Schreiner et al., "Prolonged Assisted Circulation After Heart or Aortic Surgery", *Trans. Am. Society for Art. Int. Organs*, 1963, vol. IX, pp. 182-185.
Kantrowitz et al., "Experimental Use of the Diaphragm as an Auxiliary Myocardium", *Surgical Forum*, 1958, vol. IX, pp. 266-268.
Nosé et al., "Experimental Use of an Electronically Controlled Prosthesis as an Aux. Left Ventricle", *Trans. Am. Soc. for Art. Int. Organs*, 1963, vol. IX, pp. 269-272.
Nosé et al., "Long-Term Oper. of an Electronically Controlled Plastic, Aux. Ventricle in Conscious Dogs", *Trans. Am. Soc. for Art. Int. Organs*, 1964, vol. X, pp. 140-146.
Osborn et al., "Circ. Assistance by Ext. Pulsed Pressures", *Am. Journal of Med. Electronics*, Apr.-Jun., 1964, pp. 87-90.

*Primary Examiner*—Lee S. Cohen
*Assistant Examiner*—Angela D. Sykes
*Attorney, Agent, or Firm*—Bernard L. Kleinke

[57] ABSTRACT

In a body organ control system having a pulse generator connected to a source of electrical power for generating a series of electrical timing pulses, an auxiliary pumping device is attached to a portion of the body organ for compressing and releasing it alternatingly in response to the series of timing pulses. The pumping device includes a compressor which has an opening therein for receiving and at least partially surrounding the body organ. The compressor is movable periodically to reduce substantially and forcibly the cross-sectional area of the opening by a predetermined amount to squeeze the surrounded portion of the body organ to force body materials therefrom. The pumping device includes an electrical force producing device, such as an electrical motor or a pump, which responds to the timing pulses for applying force to the compressor to cause it to reduce substantially the cross-sectional area of the opening against the force of the body organ being squeezed upon the occurrence of each one of the pulses and for releasing the compressor to permit the body organ to expand rapidly back to its unstressed normal size and shape during the time intervals between the pulses. In this manner, for example, the flow rate of a diseased heart of a person can be increased substantially, whereby the physical activities of such a person can be increased substantially.

8 Claims, 9 Drawing Figures

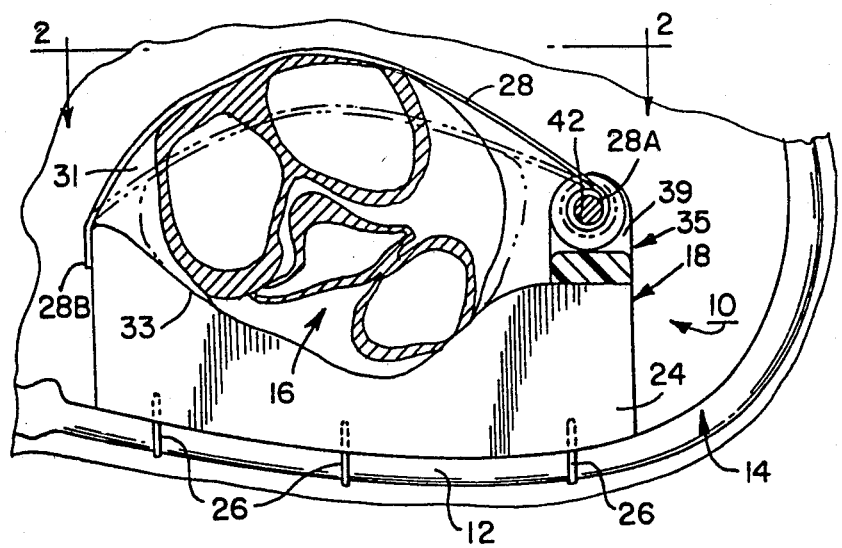
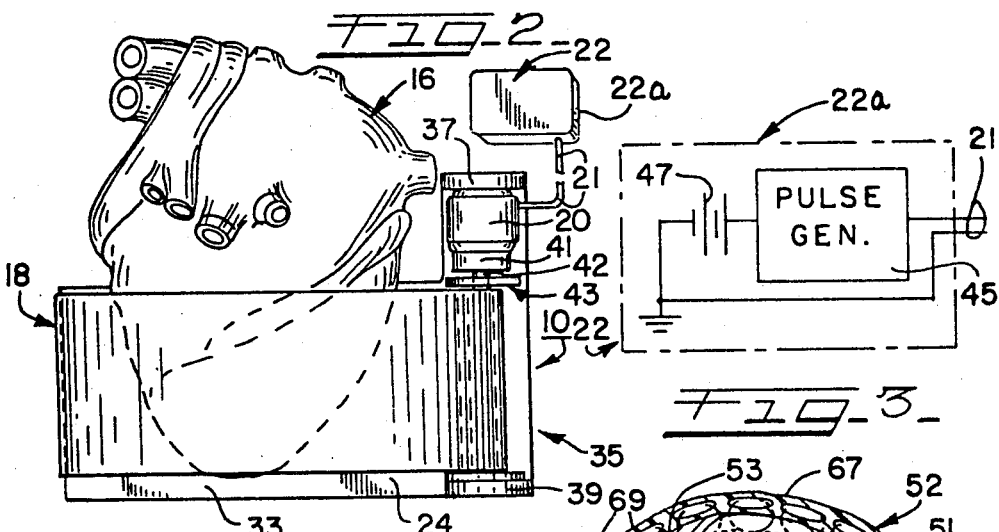
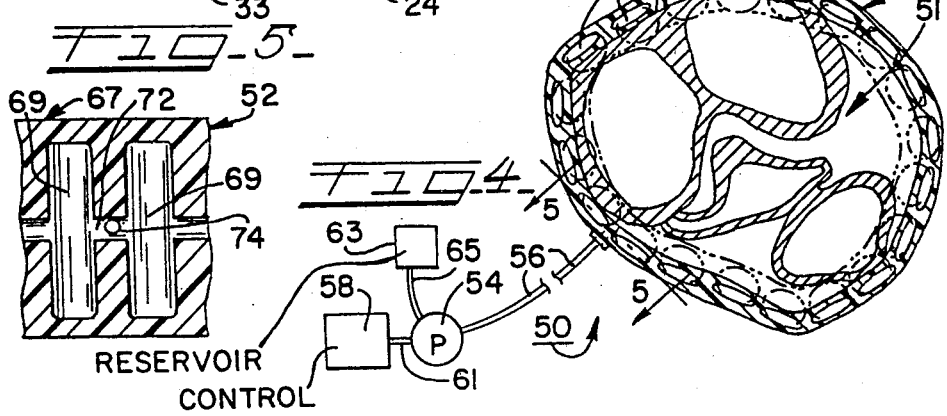

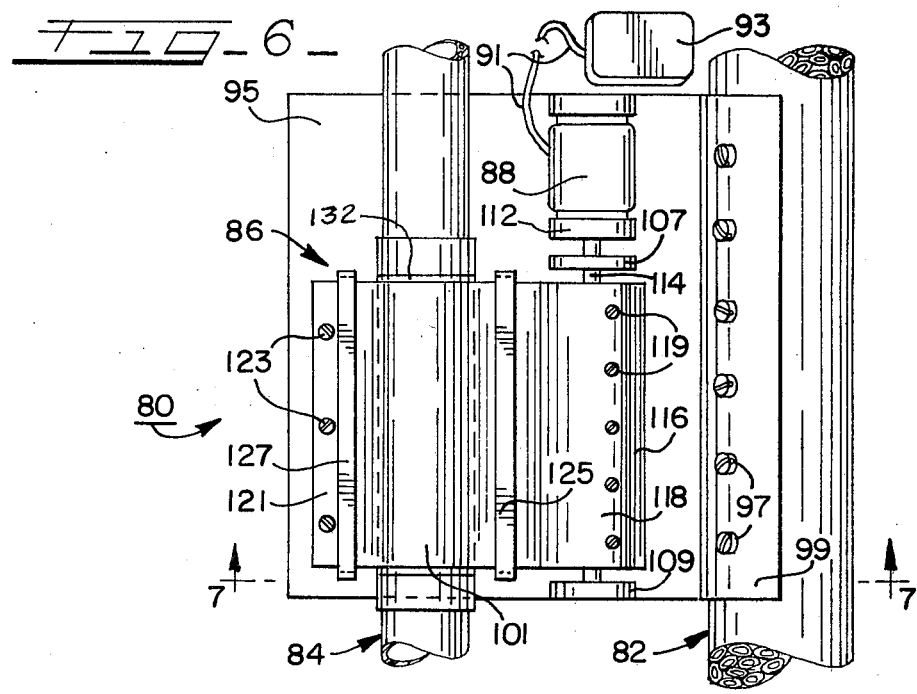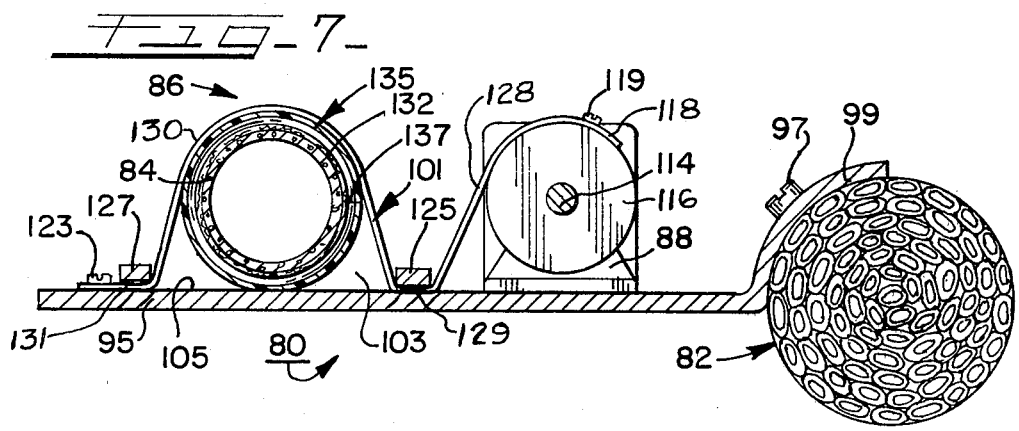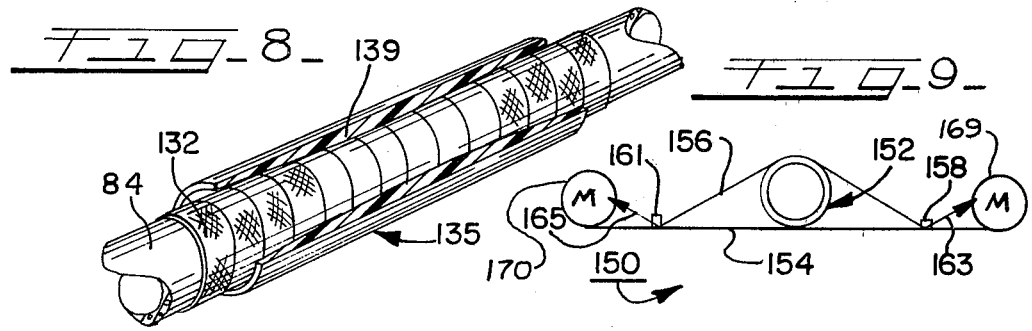

CONTROL SYSTEM FOR BODY ORGANS

This application is a continuation-in-part application of co-pending U.S. Pat. application, Ser. No. 6,034,224, filed June 30, 1979, now U.S. Pat. No. 4,304,225.

DESCRIPTION

1. Technical Field

The present invention relates in general to a control system for body organs, and it more particularly relates to a system for facilitating the functioning of a body organ, such as the assisting of the flow rate of a human heart.

2. Background Art

In the past, there have been different techniques for assisting the functioning of human organs which have ceased to function properly due to disease or other reasons, such as injuries. For example, heart pacemakers have been employed to assist the proper functioning of the heart by supplying electrical impulses to it. The present day heart pacemakers are implanted in the chest cavity and are in the form of a pulse generator which is powered by a battery to supply impulses to electrodes positioned within the heart. The electrical pulses are supplied at a predetermined rate to stimulate the heart to beat at a desired rhythm. Such heart pacemakers have been highly successful for the treatment of heart disease where there is a lack of natural stimulation of the heart from its nervous system. While heart pacemakers have proven to be highly successful for many applications, it would be highly desirable to have a new and improved control system for assisting the operation of a body organ, such as a human heart, which has ceased to function properly as a result of heart disease and has a substantially reduced flow rate. In this regard, it would be highly desirable to have a control system which would assist the human heart in its pumping operation to increase substantially its flow rate.

DISCLOSURE OF INVENTION

Therefore, it is the principal object of the present invention to provide a new and improved control system for malfunctioning body organs, which control system can assist the malfunctioning body organ to function in a more nearly normal manner.

Briefly, the above and further objects of the present invention are realized by providing in a body organ control system having a pulse generator connected to a source of electrical power for generating a series of electrical timing pulses, an auxiliary pumping device attached to a portion of the body organ for compressing and releasing it alternatingly in response to the series of timing pulses. The pumping device includes a compressor which has an opening therein for receiving and at least partially surrounding the body organ. The compressor is movable periodically to reduce substantially and forcibly the cross-sectional area of the opening by a predetermined amount to squeeze the surrounded portion of the body organ to force body materials therefrom. The pumping device includes an electrical force producing device, such as an electrical motor or a pump, which responds to the timing pulses for applying force to the compressor to cause it to reduce substantially the cross-sectional area of the opening against the force of the body organ being squeezed upon the occurrence of each one of the pulses and for releasing the compressor to permit the body organ to expand rapidly back to its unstressed normal size and shape during the time intervals between the pulses. In this manner, for example, the flow rate of a diseased heart of a person can be increased substantially, whereby the physical activities of such a person can be increased substantially.

In one form of the invention, the compressor includes a compression member having a gently curved contour for applying progressively-increasing external pressure to the part of the body being squeezed, to cause it to deform over a gradually progressively increasing area thereof. In this manner, the part of the body being squeezed is not subjected to overly severe or irregular deformations thereof which would otherwise cause injury thereto after long and repeated use of the system.

Also, for preventing or at least greatly reducing the possibility of injury to the part of the body being squeezed, between it and the compression member is interposed a protective sleeve to help distribute the pressure being applied in a uniform manner.

BRIEF DESCRIPTION OF DRAWINGS

The above mentioned and other objects and features of this invention and the manner of attaining them will become apparent and the invention itself will be best understood by reference to the accompanying description of embodiments of the invention taken in conjunction with the accompanying drawings, wherein:

FIG. 1 is a cross-sectional plan view of the control system, which is constructed in accordance with the present invention and which is shown mounted in position within a chest cavity attached to a human heart for assisting its proper functioning;

FIG. 2 is a back elevational, cross-sectional view of the control apparatus of FIG. 1 taken substantially along the line 2—2 thereof illustrating the back side of the apparatus and the heart;

FIG. 3 is a symbolic block diagram of the electrical pulse generator of the control system shown in FIG. 2;

FIG. 4 is a horizontal cross-sectional plan view of another control system, which is constructed in accordance with the present invention and which is shown mounted on a human heart;

FIG. 5 is a fragmentary cross-sectional view of a portion of the control system of FIG. 4 taken substantially along the line 5—5 thereof;

FIG. 6 is an elevational view of another control system, which is constructed in accordance with the present invention and which is shown mounted in position within a chest cavity attached to a human aorta for assisting the proper functioning of the human heart;

FIG. 7 is an enlarged-scale sectional view thereof taken substantially on line 7—7 of FIG. 6;

FIG. 8 is a pictorial view of a protective sleeve for the body part, and a compression member of the system of FIG. 6, the member being shown with a portion removed for illustration purposes; and FIG. 9 is a schematic view of still another control system, which is constructed in accordance with the present invention and which is shown mounted in position attached to a body part in a similar manner to the system of FIG. 6.

BEST MODE FOR CARRYING OUT THE INVENTION

Referring now to the drawings, and more particulary to FIGS. 1, 2 and 3 thereof, there is shown a control system 10, which is constructed in accordance with the present invention, and which is mounted on a front rib 12 within a rib cage generally indicated at 14 of a person having a malfunctioning heart 16, in order to assist its proper functioning by increasing substantially its flow rate. It will become apparent to those skilled in the art that the control system of the present invention may also be used for assisting the operation of other different body organs, such as the bladder, colon and others, to increase substantially their sluggish or nonexistent operation.

The control system 10 generally comprises a compressor 18 which surrounds the lower portion of the heart 16 and is driven by an electric motor 20 mounted thereon as shown in FIG. 2 of the drawings. An electric cable 21 supplies a series of electrical timing pulses from a control unit 22 which may be implanted in the body in a similar manner as a heart pacemaker. The timing pulses are used to turn the motor 20 on and off alternatingly, whereby the electric motor in turn causes the compessor 18 to constrict and to release alternatingly the lower portion of the heart 16 to assist the pumping operation of the heart 16. The resulting operation is similar to the conventional manually-applied cardiac pulmonary resuscitation technique of assisting the operation of a heart, in that the lower portion of the heart, where the major pumping chambers are located, it alternatingly compressed and released by means of the system 10 of the present invention to increase the flow rate of the heart 16.

Considering now the compressor 18 in greater detail with reference to FIGS. 1 and 2 of the drawings, the compressor 18 includes an elongated support block 24 which is fastened to the front rib 12 opposite the lower portion of the heart 16 by means of a series of fastening devices 26 which may be in the form of U-shaped staples or the like which surround the rib 12 and are driven into the block 24. A flexible strap 28 extends around the back side of the lower portion of the heart 16 and with the front block 24 defines an opening 31 to receive the lower portion of the heart 16. As indicated in phantom lines shown in FIG. 1 of the drawings, when the motor 20 is energized, the effective length of the strap 28 is shortened so as to reduce forcibly the cross-sectional area of the opening 31 by a predetermined amount to squeeze the surrounded portion of the heart 16 to force blood therefrom.

The block 24 is composed of suitable soft stiff material which is somewhat resilient to engage the front side of the lower portion of the heart 16 as shown in FIG. 1 of the drawings. A complementary-shaped rear wall 33 of the block 24 engages and generally conforms to the shape of the front side of the bottom portion of the heart 16. A clevis end portion 35 projects rearwardly from one end of the block 24 and includes a pair of parallel, vertically spaced-apart projections 37 and 39 for supporting the motor 20 from the underside of the upper projection 37 as best seen in FIG. 2 of the drawings. A one-way clutch 41 couples drivingly the output of the motor 20 to a vertical shaft 42 which is journaled for rotation about its opposite end in the lower projection 39. A reel 43 is fixed to the shaft 42 between the projections 37 and 39 and is driven rotatably by the motor 20.

Considering now in greater detail the control unit 22, as shown in FIG. 3 of the drawings, the control unit 22 includes a pulse generator 45 which generates a square wave pulse train which, in turn, drives the electric motor 20 for turning it on and off periodically. A battery 47 powers the pulse generator 45. The pulse generator 45 and the battery 47 are encapsulated within a housing 22a as best seen in FIG. 2 of the drawings, the housing 22a being highly corrosion resistant.

In operation, the control unit 22 generates the series of electrical timing pulses and supplies them via the cable 21 to the electrical motor 20. In response to each one of these electrical timing pulses, the motor 20 is driven into operation to rotate drivingly the shaft 42 via the one-way clutch 41. As a result, the reel 43 is rotated about its axis in a counterclockwise direction as viewed in FIG. 1 of the drawings to coil one end 28A of the strap therein, the opposite end 28B of the strap 28 being fixed to the opposite end of the block 24 by any convenient means (not shown). Thus, as indicated by the phantom lines, the effective cross-sectional area of the opening 31 defined by the strap 28 and the block 24 effectively becomes smaller in size to exert a pressure on the lower portion of the heart 16 for forcing fluid therefrom, whereby the pumping operation of the heart 16 is substantially increased. In this regard, the strap 28 forces the back side of the lower portion of the heart 16 against the rear wall 33 of the block 24 for squeezing it. The flexible strap 28 grips frictionally the back side of the lower portion of the heart during the compression operation.

At the trailing edges of the timing pulses, the electrical motor 20 is de-energized to prevent further driving of the reel 43. Once the motor 20 is turned off, the heart 16 is permitted to expand according to its normal operation, since the one-way clutch 41 permits the reel 43 to rotate in a counter-clockwise direction as viewed in FIG. 1 of the drawings and thus to permit the strap 28 to move from the phantom line position as shown in FIG. 1 of the drawings to the solid line position as indicated therein. In this regard, the end 28A of the strap moves out of the reel 43.

Once the heart has expanded back to its normal position, the next timing pulse energizes the motor 20, which in turn repeats the compressing cycle of operation.

It should be noted that the operation of the control unit 22 is an asynchronous operation to control the heart beat rhythm of the heart 16. However, it will become apparent to those skilled in the art that the control unit 22 can be made to operate synchronously in a similar manner that current heart pacemakers operate in a synchronous manner.

Referring now to FIGS. 4 and 5 of the drawings, there is shown a body organ control system 50, which is also constructed in accordance with the present invention and which is a hydraulically powered system for assisting the pumping operation of the heart 51.

The control system 50 generally comprises a tubular sleeve compressor 52 which surrounds the lower portion of the heart 51 and has an opening 53 therein for receiving snugly and grippingly the lower portion of the heart as indicated in FIG. 4 of the drawings. The hollow compressor 52 may be attached to the heart 51 by any suitable technique, such as securing it in place with sutures (not shown). A pump 54 discharges under pressure a suitable fluid, such as a saline solution, through a tube 56 to the compressor 52 for causing it to expand or inflate and thus to reduce forcibly the cross-sectional area of the opening 53, whereby the lower portion of the heart 51 is compressed to assist in its pumping operation by forcing fluids therefrom in a manner similar to the conventional manual cardiac pulmonary resuscitation technique.

The pump 54 alternatingly supplies and releases the pressure on the fluid supplied to the compressor 52. As a result, the lower portion of the heart 51 expands to help increase its flow rate. As in the case of the operation of the system 10, the heart is compressed to force fluids therefrom and alternatingly released to permit the heart to snap back resiliently to its normal unstressed condition to draw blood back therein.

An electrical control unit 58 supplies a series of electrical timing pulses via a cable 61 to the pump 54 in a similar manner as the control unit 22 supplies electrical impulses to the motor 20 for turning the compressor on and off alternatingly. A fluid reservoir 63 is connected in fluid communication with the pump 54 via a tube 65 so that, when fluid is forced out of the compressor 52 when the heart 51 expands back to its normal unstressed condition, fluid flows backwardly through the tube 56, the pump 54, the tube 65 and into the reservoir 63. The entire system 50 may thus be implanted in the chest cavity of the patient for continuous operation. Alternatively, the pump 54, the power supply control unit 58 and the reservoir 63 may be mounted externally of the chest cavity, and these units may be worn on the body, such as by attaching them to the belt of the user, whereby the tube 56 extends through a small opening (not shown) in the chest of the patient to the compressor 52.

Considering now the compressor 52 in greater detail with reference to FIGS. 4 and 5 of the drawings, the compressor 52 generally comprises a soft flexible molded sleeve unit 67 which fits snugly about the lower portion of the heart 51 and includes a series of equally spaced-apart cells or elongated chambers 69 which extend axially almost the entire axial length of the sleeve 67. The fluid flows into the cells 69 via a common passage 72 which extends circumferentially along the sleeve 67 and is disposed in fluid communication with the mid portions of the cells 69 as best seen in FIG. 5 of the drawings.

When fluid is forced into the common passage 72 via an opening 74 (FIG. 5) communicating with the tube 56, the fluid flows into each one of the cells 69 and causes it to expand. In this regard, each one of the cells 69 is normally unstressed and is generally elliptical in cross section as shown in solid lines in FIG. 4 of the drawings. When the cells 69 are inflated, they assume a generally circular cross-sectional shape as indicated in the phantom line showing in FIG. 4 of the drawings, thereby substantially reducing the cross-sectional area of the opening 53 in the sleeve 67.

Referring now to FIGS. 6, 7 and 8 of the drawings, there is shown a control system 80, which is also constructed in accordance with the present invention, and which is similar to the system 10, except that the system 80 is mounted on a vertebrae 82 within the body of the person having a malfunctioning heart (not shown) and compresses an aorta 84 repeatedly to increase the blood flow rate substantially. The system 80 squeezes the aorta 84 periodically, in synchronism with the heart beat of the body in a similar manner as the system 10 compresses its body part. The system 80 causes blood to be propelled from the aorta 84 in accordance with counterpulsation techniques, which are disclosed in an article entitled, "The Evolution of Counterpulsation Techniques", by William C. Birtwell, et al, in a publication entitled *Medical Instrumentation*, Vol. 10, No. 5, 1976.

A single size of the system 80 is adapted to fit substantially all adult patients, since the aorta is generally of a uniform size and length for adult persons. By applying pressure to the outside of the aorta, the system 80 does not come into contact with the blood, and thus there is no risk of contamination of the blood. Also, the system 80 is compact in size and is implantable for long term use of the system. With the system 80, as well as the other systems disclosed herein, no permanent anatomical changes are required, and the installation is relatively uncomplicated and can be performed in a relatively short time.

The control system 80 generally comprises a compressor 86 which surrounds the portion of the aorta 84 and is driven by an electrical force producing means including an electric motor 88. An electric cable 91 conveys a series of electrical timing pulses from a control unit 93, which may be implanted in the body and which is similar to the unit 22 of FIG. 2. The timing pulses are used to turn the motor 88 on and off alternatingly in synchronism with the heart beat, whereby the electric motor 88, in turn, causes the compressor 86 to constrict and release alternatingly the surrounded portion of the aorta 84 to assist the pumping operation of the heart in accordance with conventional counterpulsation technques. Thus, the flow rate of the heart is increased accordingly.

In operation, the aorta 84 is squeezed or compressed during the time when the ventricles (not shown) of the heart are resting. This is accomplished by at least partially flattening the aorta to increase the pressure of the blood at both sides of the compressed area of the aorta. Thus, greater blood flow occurs downstream of the compressed area to adhieve the desired result. As an additional advantage, greater blood flow occurs back toward the heart and into the coronary arteries (not shown) to increase the nourishment of the heart. It should be noted that the back flow of blood is prevented from entering the left ventricle due to the aortic valve which is closed during this portion of the heart beat.

Referring to FIGS. 6 and 7 of the drawings, the compressor 86 includes a support member or backing plate 95. A series of fastening devices or screws 97 attach an apertured arcuate end portion or flange 97 of the support member 95 to the vertebrae 82. Thus, the support member 95 is cantilevered forwardly from the vertebrae 82 to a position opposite the downwardly extending aorta 84 below the heart (not shown). A flexible strap 101, which is similar to the flexible strap 28 of the system 10, is attached to the backing member 95 to form an opening 103 which receives the aorta 84 positioned between the strap 101 and a rear wall 105 of the support member 95.

In order to tension the strap 101 for decreasing the size of the opening 103, and thus to at least partially flatten the aorta 84 for propelling blood therealong, the motor 88 pulls the strap 101 in a similar manner as the motor 20 tensions the strap 28 of the system 10. For this purpose, the motor 88 is mounted on the vertically extending rear wall 105 of the support member 95 between the aorta 84 and the arcuate end portion 97. A pair of oppositely-disposed, parallel spaced-apart projections 107 and 109 extend from the face of the rear wall 105 of the support member 95 and support an axle 114 of a roller 116 for rotation therebetween. A one-way clutch 112 connects drivingly the output shaft of the motor 88 to the axle 114 for rotating the roller 116 about its axis between the projections 107 and 109.

For the purpose of tensioning the strap 101 when the motor 88 is activated, one end 118 of the strap 101 is attached by means of a series of screws 119 to the roller 116. An opposite end 121 of the strap 101 is connected by means of screws 123 to the outer end portion of the backing member 95. As best seen in FIG. 7, from the inner end 118 of the strap 101 fastened to the roller 116, an intermediate portion 128 of the strap extends to the wall 105 under a generally U-shaped hold-down bar 125 fixed to and projecting from the wall 105. An aorta encircling portion 130 of the strap extends between the hold-down portion 129 under the hold-down bar 125 and a hold-down portion 131 under another generally U-shaped hold-down bar 127, and defines with the adjacent portion of the wall 105, the aorta receiving opening 103.

When the motor is energized, the roller 116 rotates about its axis to wind up the inner end 118 of the strap 101 to tension it. In this manner, the effective area of the opening 103 is decreased to compress the aorta 84 for counterpulsation purposes. By tensioning the strap 101, the effective length of the aorta encircling portion 130 between the hold-down bars, is decreased to apply pressure to the adjacent portion of the aorta against the rear wall 105 in a manner similar to the strap 28 and the rear wall 33 of the control system 10.

The control unit 93 then deenergizes the motor 88 to release the tension applied to the strap 101, whereby the aorta 84 expands radially outwardly back to its normal configuration. Thereafter, the operation is repeated in a similar manner as the control system 10.

In order to help distribute the pressure applied to the aorta, a protective sleeve 132 is disposed about the aorta 84. The protective sleeve 132 is generally tubular in configuration and has a pair of opposite open ends. The protective sleeve 132 is composed of thin, pliable material which is easily compressible and yet distributes the pressure uniformly over the aorta outer surface.

As shown in FIG. 8 of the drawings, the protective sleeve 132 is composed of a mesh tape wrapped about and in direct contact with the aorta 84. For further information concerning the mesh material, reference may be made to an article entitled "Wall Reinforcement with Highly Porous Dacron Mesh in Aortic Surgery", by Tatsuzo Tanabe, M.D., in *Annuls of Surgery*, April 1980, Vol. 191, No. 4, pages 452–455.

The sleeve 132 provides for aortic wall reinforcement to help prevent aortic aneurysm. The Dacron mesh material is highly porous and is pliable so as to distribute uniformly pressure applied to the aorta.

For the purpose of preventing the aorta from being subjected to overly severe or irregular deformations thereof during the compression operation, a compression member 135 surrounds the protective sleeve 132, so that it is interposed between the compression member 135 and the aorta 84. The compression member is generally tubular in shape and is composed of resilient material. The compression member has a pair of opposite open ends and has a longitudinal slit 137 (FIG. 7) extending from end to end to enable the compression member 135 to be opened longitudinally and fitted about the wrapped aorta.

The compression member 135 has an interior hourglass configuration. In this regard, as shown in FIG. 8, the compression member 135 has a generally curved interior contour for applying progressively-increasing external pressure to the aorta 84 to cause it to deform over a gradually progressively increasing area thereof during the applying of pressure to the aorta by the strap 101. In this regard, as shown in FIG. 8, the compression member 135 includes a thick protruding mid portion 139 and is tapered gradually and smoothly from the mid portion 139 to the outer ends thereof. The compression member 135 is composed of suitable molded, flexible, thermoplastic material, such as the material sold under the trade name "Silastic", by DuPont. The strap 101 may also be composed of "Silastic" material.

Referring now to FIG. 9, there is shown a control system 150, which is also constructed in accordance with the present invention. The control system 150 is similar to the system 80 in that the system 150 is used to compress an aorta 152 in accordance with counterpulsation techniques, except that the system 150 applies pressure directly toward its support member 154, which is similar to the backing member 95 of the system 80.

The system 150 includes a strap 156 which is similar to the strap 101 and receives the aorta 152 between the strap 156 and the backing member 154. A pair of generally U-shaped hold-down bars 158 and 161 extend transversely across the strap 156 in a similar manner as the hold-down bars 125 and 127 of the system 80. A pair of opposite ends 163 and 165 of the strap 156 are connected to a pair of electrical force producing motors 169 and 170 in a similar manner as the motor 88 of the system 80. In this manner, during compression of the aorta 152, the motors 169 and 170 rotate in the opposite directions to pull the strap ends 163 and 165 in opposite directions as indicated by the arrows to apply oppositely-directed tension on the strap 156, thereby resulting in the application of pressure to the aorta directed toward the support member 154. In this manner, the aorta does not tend to rotate or twist during operation as could occur under some conditions in the one-way strap pulling system 80. It is to be understood that the system 150 includes a protective sleeve (not shown) and a compression member (not shown) similar to the protective sleeve and compression member of the system 80.

As shown in FIG. 9, the hold-down bars 158 and 161 are spaced further apart relative to the aorta 152 as compared to the hold-down bars 125 and 127 of the system 80, to provide a greater space between the hold-down bars for the purpose of more completely flattening the aorta 152. In this regard, there is provided a greater amount of space between the hold-down bars 158 and 161 to permit a more complete deformation of the aorta 152, against the support member 154.

It is to be understood that the system 150 also includes, in addition to the motors 169 and 170, one-way clutches (not shown) and rollers (not shown) for tensioning the strap 156 in a similar manner as the clutches and rollers tension the strap 101 of the system 80. By employing two separate pairs of force producing motors, clutches and rollers, the system 150 can continue to function, even if one of the force producing means should malfunction. Thus, an inherent fail-safe arrangement is provided.

While particular embodiments of the present invention have been disclosed, it is to be understood that various different modifications are possible and are contemplated within the true spirit and scope of the appended claims. For example, in the appended claims, the use of the word "body part" can refer to an organ, such as the heart, colon, lung or others; or it can mean a vessel, such as the aorta. Moreover, the term "body part" as used in the appended claims can refer to an artificial body part, such as a tube (not shown) sewn in line with the aorta. Also, a part or all of the control system may be implantable, and in this regard, the compressor is totally implantable and the force producing means may either be implantable or worn on the person exteriorly as will become apparent to those skilled in the art. There is no intention, therefore, of limitations to the exact abstract or disclosure herein presented.

I claim:

1. A body organ control system, comprising:

auxiliary pumping means including compression means adapted to be implanted totally within the body for applying pressure to the outer surface of a body part to compress it repeatedly and thus to force body materials therefrom;

control means for producing a series of timing pulses;

electrical force-producing means connected to said compression means and responsive to said series of timing pulses for causing said compression means to apply pressure to the outer surface of the body part only upon the occurrence of individual ones of said pulses;

said compression means including a compression member having a gently curved contour, said member having a thick portion for engaging the outer surface of the body part and for applying progressively-increasing external pressure to the body part to cause it to deform over a gradually progressively increasing area thereof during the applying of pressure to the body part by said compression means wherein the body part is the aorta and said compression means includes support means adapted to be fixed directly to and to engage directly another internal body part of the body near said aorta, said support means having a rear wall adapted to be secured to the aorta body, fastening means adapted for attaching fixedly said support means directly to and in engagement with said another internal body part disposed within the body for anchoring purposes, elongated strap means connected at its ends to said support means to cooperate with said rear wall of said support means to receive the aorta for applying pressure thereto, and said force producing means applying force repeatedly to said strap means to tension it repeatedly and thus to cause said pressure to be applied repeatedly to the surrounded outer part of the aorta against said support means.

2. A body organ control system according to claim 1, wherein said thick portion of said compression member includes a thick protruding mid portion, said member being tapered gradually and smoothly from said mid portion to outer ends thereof.

3. A body organ control system according to claim 2, wherein said compression member is generally tubular in shape, is adapted to surround the body part, is composed of resilient material, has a pair of opposite open ends, and is slit longitudinally from one open end to the opposite open end.

4. A body organ control system according to claim 1, further including outer protective sleeve means adapted to be interposed between said compression member and the body part to help distribute said pressure uniformly to the outer surface of the body part.

5. A body organ control system according to claim 4, wherein said protective sleeve means is generally tubular in shape, has a pair of opposite open ends, and is composed of thin pliable material.

6. A body organ control system according to claim 5, wherein said material includes a mesh tape adapted to be wrapped about and in direct contact with the body part.

7. A body organ control system according to claim 1, wherein said force producing means applies oppositely-directed forces to opposite end portions of said strap means.

8. In a body control organ system having control means for generating a series of electrical timing pulses, the combination comprising:

auxiliary pumping means including compression means adapted to be implanted totally within the body for applying pressure to the outer surface of a body part to compress it repeatedly and thus to force body materials therefrom;

said compression means including a compression member having a gently curved contour, said member having a thicker portion for engaging the outer surface of the body part and for applying progressively-increasing external pressure to the outer surface of the body part to cause it to deform over a gradually progressively increasing area thereof during the applying of pressure to the body part by said compression means:

electrical force-producing means responsive to said series of timing pulses for causing said compression means to apply said pressure to said outer surface of the body part upon the occurrence of individual ones of said pulses wherein the body part is the aorta and said compression means includes support means adapted to be fixed directly to and to engage directly another internal body part of the body near said aorta, said support means having a rear wall adapted to be secured to the aorta body, fastening means adapted for attaching fixedly said support means directly to and in engagement with said another internal body part disposed within the body for anchoring purposes, elongated strap means connected at its ends to said support means to cooperate with said rear wall of said support means to receive the aorta for applying pressure thereto, and said force producing means applying force repeatedly to said strap means to tension it repeatedly and thus to cause said pressure to be applied repeatedly to the surrounded outer part of the aorta against said support means.

* * * * *